United States Patent [19]
Faubl et al.

[11] 3,980,648
[45] Sept. 14, 1976

[54] PROCESS FOR PRODUCING QUINOXALINE-DI-N-OXIDES

[75] Inventors: Hermann Faubl, Mystic; Banavara Lakshmana Mylari, Waterford, both of Conn.

[73] Assignee: Pfizer Inc., New York, N.Y.

[22] Filed: Mar. 12, 1975

[21] Appl. No.: 557,531

Related U.S. Application Data

[63] Continuation-in-part of Ser. No. 349,805, April 10, 1973, abandoned.

[52] U.S. Cl. ............................................. 260/250 Q
[51] Int. Cl.² ........................................ C07D 241/52
[58] Field of Search ............................... 260/250 Q

[56] References Cited
UNITED STATES PATENTS

| | | | |
|---|---|---|---|
| 3,493,572 | 2/1970 | Johnston | 260/250 Q |
| 3,558,624 | 1/1971 | Ley et al. | 260/250 Q |
| 3,600,388 | 8/1971 | Durckheimer | 260/250 Q |

OTHER PUBLICATIONS

Morrison et al., *Organic Chemistry*, 1968, pp. 633, 640–641.
March, *Advanced Organic Chemistry*, pp. 674–675.

*Primary Examiner*—Nicholas S. Rizzo
*Assistant Examiner*—David E. Wheeler
*Attorney, Agent, or Firm*—Connolly and Hutz

[57] ABSTRACT

A process for the preparation of methyl 3-(2-quinoxalinylmethylene)carbazate $N^1,N^4$-dioxide which comprises contacting a 2-quinoxalinecarboxaldehyde $N^1,N^4$-dioxide nitrone with at least about an equimolar proportion of methyl carbazate in acidic solvent medium until reaction is substantially complete.

2 Claims, No Drawings

3,980,648

PROCESS FOR PRODUCING QUINOXALINE-DI-N-OXIDES

CROSS REFERENCE TO RELATED APPLICATIONS

This application is a continuation-in-part of U.S. patent application Ser. No. 349,805 filed on Apr. 10, 1973, now abandoned This invention relates to a novel synthetic procedure and more particularly to a novel method for the preparation of methyl 3-(2-quinoxalinylmethylene)carbazate $N^1,N^4$-dioxide. The compound prepared by the novel subject process is well known as a urinary tract antiseptic, systemic anti-infective, animal growth promotant as an agent for the control of chronic respiratory diseases in poultry and improvement of feed efficiency in animals. (*Australian Vet. J.* 48, No. 10 579, (1972) and *Rec. Med. Vet.* ecole Alfort 148 No. 3 365-73 (1972)).

SUMMARY OF THE INVENTION

Accordingly the present invention discloses a process for the preparation of methyl 3-(2-quinoxalinylmethylene)carbazate $N^1, N^4$-dioxide which comprises contacting a 2-quinoxalinecarboxaldehyde $N^1,N^4$-dioxide nitrone with at least about an equimolar proportion of methyl carbazate in acidic solvent medium until reaction is substantially complete.

Especially preferred is the above process wherein the reaction temperature is from about 90°–100°C.

DETAILED DESCRIPTION OF THE INVENTION

The new reaction of the present invention is carried out in a reaction-inert solvent. An inert solvent for purposes of this invention contemplates any solvent which allows solubilization of the reactants and is free of adverse effect on the reagents and products under the conditions employed. Two preferred types include organic acids, such as acetic acid, and lower alcohols and esters such as ethanol and ethyl acetate. The novel reaction of the present invention requires the presence of a strong acid catalyst. Examples of such acids suitable for this purpose are hydrochloric acid, hydrobromic acid, sulfuric acid, phosphoric acid, p-toluenesulfonic acid and trifluoroacetic acid. It is usually satisfactory to employ from about 2–10% by weight of the total reaction mixture of the acid catalyst. (If a strong acid e.g. trifluroacetic acid is used for a reaction solvent an acid catalyst is unnecessary). Often the presence of a small quantity of water in the reaction mixture is desirable and this may be conveniently introduced by employing as an acid catalyst such acids as concentrated hydrochloric or hydrobromic acid which contain water. However, any solvent possessing the qualities set forth above will be satisfactory. Those skilled in the art will appreciate that any temperature at which the reaction proceeds without extensive decomposition is satisfactory however, the preferred reaction temperature is 90°–100°C. although optimum temperature may vary with the choice of nitrone. The higher temperature ranges may require the use of an autoclave or other high-pressure vessel.

Depending upon the particular reagents and temperature, the reaction time can vary from a few minutes to as long as 24 hours. Generally, the ensure complete reaction the relatively long time periods are preferred. Optimum reaction conditions are readily determined by experiment.

The proportion of quinoxaline derivative relative to the carbazate may vary widely but for efficient conversion at least about one equivalent of carbazate per mole of quinoxaline derivative is necessary and a molar excess of 50–100% of the carbazate is preferred.

The starting materials for the process of the present invention are readily prepared by well known standard organic chemical techniques. For example the nitrones are prepared via the route described by H. K. Kim, U.S. Pat. No. 3,644,363. The methyl carbazate and its derivatives are available through the sequence described by N. Rabjohn and H. D. Barnstorff, *J. Am. Chem. Soc.*, 75, 2259 (1953).

The product is isolated by dilution of the reaction mixture with water, cooling and subsequent filtration. The solid thus collected is washed with water and dried to provide the desired methyl-3-(2-quinoxalinylmethylene)carbazate $N^1,N^4$-dioxide.

The valuable product of this invention exhibits activity as urinary tract systemic anti-infective in animals, including man, against a wide variety of microorganisms including Gram-positive and Gram-negative bacteria. It is especially valuable against Gram-negative infections both in vitro and in vivo.

Further, the addition of a low level of the herein described Schiff base to the diet of animals, both ruminant and non-ruminant, such that these animals receive the product over an extended period of time, at a level of from about 0.04 mg/kg. to about 10 mg/kg. of body weight per day, especially over a major portion of their active growth period, results in an acceleration of the rate of growth ad improved feed efficiency. Included in these two classes of animals are poultry (chickens, ducks, turkeys), cattle, sheep, dogs, cats, rats, swine, mice, horses, goats, mules, rabbits, mink, etc. The beneficial effects in growth rate and feed efficiency are over and above what is normally obtained with complete nutritious diets containing all the nutrients, vitamins, minerals and other factors known to be required for the maximum healthy growth of such animals. The animals thus attain market size sooner and on less feed.

These feed compositions have been found to be particularly valuable and outstanding in the case of such animals as poultry, rats, hogs, swine, lambs, cattle, and the like. In some instances the degree of response may vary with respect to the sex of the animals. The products, may, of course, be administered in one component of the feed or they may be blended uniformly throughout a mixed feed; alternatively as noted above, they may be administered in an equivalent amount via the animal's water ration. It should be noted that a variety of feed components may be of use in the nutritionally balanced feeds.

The following examples are merely illustrative and in no way limit the scope of the appended claims.

EXAMPLE I

To a solution of 43.8 g, (0.20 mol) N-methyl-α-(quinoxalinyl-methylene) nitrone $N^1,N^4$-dioxide and methyl carbazate (27 g, 0.30 mol) in acetic acid (400 ml) is added concentrated sulfuric acid (20 ml). The resulting mixture is heated at about 90°–100°C for about 20–24 hours. After cooling and dilution with water (1200 ml), the precipitated solid is collected and dried to give methyl 3-(2-quinoxalinylmethylene)carbazate $N^1,N^4$-dioxide.

EXAMPLE II

To acetic acid (20 ml) was added N-methyl-2-(2-quinoxaline-$N^1,N^4$-dioxide)-nitrone (2.19g, 0.01 mol), methyl carbazate (1.35g, 0.015 mol) and conc. sulfuric acid (1 ml). The mixture was heated at 90°–100°C for 20 hrs. then cooled and diluted with 60 ml of water and filtered to give methyl 3-(2-quinoxalinylmethyline)carbazate-$N^1,N^4$-dioxide (2.2g, 84%) as a light yellow solid mp. 248°–250° (d). Mass spec, NMR and IR consistent with assigned structure.

EXAMPLE III

A mixture of acetic acid (19 ml), conc. HCl(0.7 ml) and N-(p-dimethylaminophenyl)-2-(2-quinoxalinyl-$N^1,N^4$-dioxide)-nitrone (2.85g, 0.0088 mol) was stirred at room temperature for 30 min. and then filtered. To the filtrate, was added methyl carbazate (1.23g, 0.0131 mol) and the reaction heated at 55° for 2 hrs. and then stirred at room temperature overnight. The mixture filtered, washed with water and methanol, dried to give methyl 3-(2-quinoxalinyl methylene)carbazate-$N^1,N^4$-dioxide (1.79g, 78%) as a dark solid (tan → yellow) mp 242° (d) IR, NMR and mass spec are consistent with assigned structure.

What is claimed is:

1. A process for the preparation of methyl 3-(2-quinoxalinylmethylene)carbazate $N^1,N^4$-dioxide which comprises the step of reacting a 2-quinoxalinecarboxaldehyde $N^1,N^4$-dioxide nitrone with an equimolar proportion of methyl carbazate in a reaction-inert solvent inthe presence of a strong acid catalyst selected from the group consisting of hydrochloric acid, hydrobromic acid, sulfuric acid, phosphoric acid, p-toluenesulfonic acid and trifluoroacetic acid.

2. The process of claim 1 wherein said process is conducted at a reaction temperature of from about 90°–100°C.

* * * * *